United States Patent [19]

Hoffman

[11] Patent Number: 5,273,033

[45] Date of Patent: Dec. 28, 1993

[54] ELECTRICAL STIMULATION FOR TREATMENT OF OSTEOARTHRITIS

[75] Inventor: Kent C. Hoffman, Parkton, Md.

[73] Assignee: Murray Electronics Associates Limited Partnership, Hunt Valley, Md.

[21] Appl. No.: 762,346

[22] Filed: Sep. 19, 1991

[51] Int. Cl.$^5$ .............................................. A61N 1/18
[52] U.S. Cl. ....................................... 607/46; 607/72
[58] Field of Search .................... 128/421, 419 R, 422

[56] References Cited

U.S. PATENT DOCUMENTS

| | | | |
|---|---|---|---|
| 3,881,494 | 5/1975 | Paul | 128/421 |
| 3,902,502 | 9/1975 | Liss et al. | 128/422 |
| 4,632,117 | 12/1986 | James | 128/421 |
| 4,944,949 | 7/1990 | Story et al. | 424/451 |
| 4,997,850 | 3/1991 | Kimura et al. | 514/544 |

OTHER PUBLICATIONS

*Journal of Orthopedic Research,* "Pulsing Direct . . . Osteochondral Defects", Lippiello et al, vol. 8, No. 2, 1990, pp. 266-275 Four page Stimset sales brochure, 1982.
Neuromod-Comfort Burst publication by Medtronic, 1981, 23 pages.
*Pain,* 11 (1981) 233-240 "Treatment of Osteoarthritis of the Knee with Transcutaneous Electrical Nerve Stimulation", Taylor et al.
*Physiotherapy,* Aug. 1983, vol. 69, No. 7, "TNS and Osteo-arthritic pain" Smith et al, pp. 266-268.
*Current Medical Research and Opinion,* vol. 11, No. 1, 1988, "Controlled-release naproxen . . . osteoarthritis", Frankhof, pp. 28 through 33.
*Clinical Therapeutics,* vol. 9, Suppl. C. 1986, "Efficacy of Diflunisal versus Naproxen in Osteoarthritis of the Knee . . . ", Deal et al. 13 pages.
Statistical Review and Evaluation of Voltaren (NDA 19-201), Mar. 25, 1988, 14 pages.
"Piroxicam and Osteoarthritis: A Controlled Study", Zizic et al., pp. 71-81.
*Clinical Electrophysiology,* Chapter 6, Electrical Stimulation for Pain Modulation, Mackler et al., 1989, pp. 205-215.
*Pain,* 11 (1981) 37-47, "Examination of Electrode Placements and Stimulating . . . Transcutaneous Electrical Nerve Stimulation (TENS)", Wolf et al, DYNEX Neurostimulator publication, 16 pages.
*Annals of Theumatic Diseases,* 1984, 43, 47-49, "Transcutaneous electrical nerve stimulation in osteoarthrosis . . . ", Lewis et al, pp. 47-49.
*Arch Phys Med Rehabil,* vol. 63, Dec. 1982, "Transcutaneous Nerve Stimulation in Rheumatoid Arthritis", Kumar et al, pp. 595 and 596.
*Pain,* 6 (1979) 329-334, "The Analgesic Effect of Transcutaneous Electrical Nerve Stimulation . . . with Rheumatoid Arthritis . . . " Mannheimer et al.
*New Zealand Medical Journal,* Mar. 9, 1983, "Transcutaneous electrical nerve stimulation in rheumatoid arthritis", Abelson et al., pp. 156-158.
*Scand J Rheumatology,* 7:13-16, 1978, "The Effect of Transcutaneous . . . Joint Pain in Patients with Rheumatoid Arthritis", Mannheimer et al.
*American Journal of Physical Medicine & Rehabilitation,* 1990, "Can Trials of Physical Treatments be Blinded?", Deyo et al, pp. 6-10.

*Primary Examiner*—William E. Kamm
*Assistant Examiner*—Scott M. Getzow
*Attorney, Agent, or Firm*—Nixon & Vanderhye

[57] ABSTRACT

A method and apparatus for treating osteoarthritis symptoms including pain, joint stiffness, limitation of range of motion and limitation of overall function through the use of subsensory unidirectional voltage pulses in the frequency range of 90 to 110 hertz applied to non-invasive conductive electrodes in contact with a patient's skin proximal to an arthritic joint.

13 Claims, 3 Drawing Sheets

ELECTRICAL STIMULATION FOR TREATMENT OF OSTEOARTHRITIS

FIELD OF THE INVENTION

The invention relates to a method and apparatus for the treatment of osteoarthritis.

BACKGROUND OF THE INVENTION

Osteoarthritis or osteoarthrosis is a degenerative joint disease which commonly affects both axial and peripheral diarthrodial joints in humans. Moreover, since the incidence of this disease increases steadily with age, it is an almost universal occurrence in the elderly.

Pathological characteristics of osteoarthritis include progressive deterioration and loss of articular cartilage from the surfaces of joints, as well as reactive changes at the joint margins and the underlying bone. Manifestations of the disease that are treatable are joint pain, stiffness and limitation of motion. Synovitis or joint inflammation is also a common secondary manifestation of the disease that is also treatable. Although, as aforementioned, high incidence of the disease occurs in the elderly, the treatment is highly individualized and may include (a) prescription of a pharmacological agent, (b) a surgical procedure, or (c) a physical modality.

Conventionally, patients exhibiting symptomatic osteoarthritis are initially treated by their physician by the administration of a nonsteroidal anti-inflammatory drug (NSAID). As indicated by U.S. Pat. No. 4,997,850 issued to Kimura et al and U.S. Pat. No. 4,944,949 issued to Story et al, many such nonsteroidal anti-inflammatory drugs are known and are frequently effective in reducing the symptoms of osteoarthritis. That is to say, they have demonstrated value in helping &:o relieve pain, improve activity levels, and in some cases improve function in osteoarthritic patients. Many members of this class of drugs have been approved by the U.S. Food and Drug Administration for the treatment of osteoarthritis.

None of these drugs, however, have been proven in carefully controlled clinical trials to reverse the long term natural history of this degenerative joint disease. Moreover, while many of these drugs have demonstrated effectiveness in treating the symptoms of osteoarthritis, they also have been associated with significant toxicities and other risks, such as deleterious effects on cartilage when used over prolonged periods of time. In March of 1989, for example, the U.S. Food and Drug Administration moved to warn both doctors and the public about the use of such drugs which were said to have become the No. 1 cause of complications among all prescription drugs. Moreover, in addition to being very expensive the toxicities of such drugs limit their usefulness, particularly in elderly patients.

In this regard, the above noted patent to Story et al recognizes that nonsteroidal anti-inflammatory drugs are the drugs of choice for various forms of inflammatory arthropathy including osteoarthritis, but that their prostaglandin inhibiting property responsible for their effectiveness may also be responsible for reducing the protective effects of prostaglandin on gastrointestinal mucosa. Story et al indicate that conventional enteric coatings applied over such drugs have not been fully effective and thereafter it is said that they have discovered that the use of micelles enables a particularly appropriate form of such nonsteroidal anti-inflammatory drugs to be achieved.

A second form of treating osteoarthritis involves surgery including non-replacement as well as joint replacement procedures. The latter procedures are usually offered only after non-operative as well as non-replacement surgical measures have been exhausted. Such surgical procedures as currently used vary greatly as to complexity, cost, success rate and risk, and in many respects are not alternative therapies vis-a-vis pharmacological agents and physical modalities.

The third major known form of treatment for osteoarthritis; namely, physical modalities, are useful in reducing pain and/or restoring function, particularly in patients for whom pharmacological agents have either been minimally effective or have been poorly tolerated. Although this general form of treatment would include simple bed rest, traction and heat treatment, among other things, the most widely studied is that of modifying pain perception via electrical nerve stimulation using noninvasive transcutaneous electrical nerve stimulators (TENS).

Pain modulation or control of pain by electrical stimulation is conventionally accomplished in three ways; namely, (1) sensory level stimulation, (2) motor level stimulation, and (3) noxious-level stimulation. As to the first, which is the most widely recognized and studied, electrical stimulation is delivered at or above a level felt by the patient but below motor level threshold. Such sensory level stimulation is generally obtained with low level pulses in the frequency range of 50-100 hertz with pulse widths in the range of 2-50 microseconds. Such sensory level stimulation is for the purpose of stimulating or activating only the largest diameter superficial nerve and is generally effective in the relief of acute pain problems.

Motor level stimulation, which by definition produces muscle contraction, is most often used clinically with chronic pain patients. Such motor level stimulation is generally accomplished in a frequency range of 2-4 hertz with pulse widths greater than 150 microseconds and intensities high enough to produce a strong visible muscle contraction.

Noxious level stimulation will produce a painful stimulus at the pain site or a site remote from the pain site and is generally accomplished in the frequency range of 1-5 hertz or greater than 100 hertz with long pulse durations of up to 1 second and at intensities which produce painful sensory stimulation with or without muscle contraction. Such stimulation may cause a quick onset of pain relief identified as "hyperstimulation analgesia".

Substantially all commercially available transcutaneous electrical nerve stimulators (TENS) can produce stimulation at each of the aforementioned levels, and several are marketed with instructions for using the device at each of the noted levels by way of adjustment of current, voltage or other delivery characteristics.

Exemplary prior art transcutaneous electrical nerve stimulators may be found in U.S. Pat. No. 3,881,494 to Paul et al and U.S. Pat. No. 3,902,502 to Liss. The Paul et al device is said to be provide temporary pain relief to arthritic patients when the level of current used in the treatment is the maximum level the patient can comfortably endure. Liss, on the other hand, discloses a device for producing a one-way low current at a frequency of 20 kilocycles to 1 megacycle with an on duty cycle of 75% modulated at 10-40 hertz. It is said that the apparatus with the electrodes properly positioned along nerves provides a nerve stimulator, which, although battery powered, employs a small current that often requires a viewing of the meter to be sure that treatment is in process. A manual control is provided whereby the patient may reduce the input to tolerable levels until repeated use builds up a conditioning acceptance. It is additionally indicated that the current flow is applied to give a pumping action to the nerve train between the applied contact points, and the impedance of the patient is compensated by the constant current circuit which is automatically readjusted to the needs of the patient.

Most commercially available transcutaneous electrical nerve stimulators are current sourced and have a common goal in addition to pain relief of comfortable treatment so as to reduce apprehension as to the electrical aspect of the treatment. Conventionally, the patient using such devices is instructed to slowly advance the amplitude control until the electrical stimulation is felt with subsequent higher settings used as the patient becomes accustomed to the stimulation. As demonstrated by such devices, electrical stimulation employed in the form of transcutaneous electrical nerve stimulators is a potentially important physical modality for the treatment of pain in a broad variety of medical problems. Although a number of such devices have indications pertaining to effective pain treatment under the broad term of arthritis and a few include osteoarthritic pain, such prior devices have not been carefully clinically studied or consistently employed to directly treat still other important aspects of osteoarthritis, such as joint stiffness, range of motion and function.

Accordingly, it is the primary object of the present invention to employ a method and apparatus having demonstrated statistically significant improvement for all of the primary clinical measures of osteoarthritis. Such measures include independent clinical measures of joint stiffness, range of motion and overall function in addition to reduction in pain. More specifically, I have discovered a method and apparatus for the treatment of the broader aspects that define osteoarthritis by using electrical stimulation at a subsensory level whereby the amplitude of the voltage source signal is first adjusted to provide a slight sensation to the patient and thereafter immediately reduced to a subsensory level for the duration of the treatment. Such treatment has been clinically shown in carefully controlled double-blinded trials to reduce osteoarthritis joint pain, improve the range of joint motion, reduce morning stiffness and improve joint function as judged by the patient, as well as a physicians global evaluation in five medical centers.

BRIEF DESCRIPTION OF THE DRAWINGS

These, as well as other objects and advantages of this invention will be more clearly appreciated by carefully studying the following detailed description of a presently preferred exemplary embodiment of this invention in conjunction with the accompanying drawings in which.

DETAILED DESCRIPTION OF THE DRAWINGS

Figure 1:
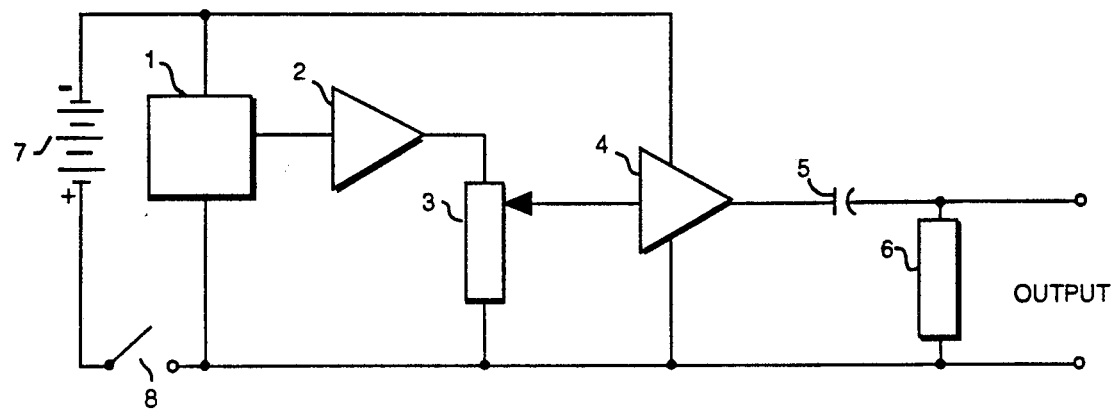
FIG. 1 is a block diagram of an exemplary electrical stimulator apparatus.
Figure 3:
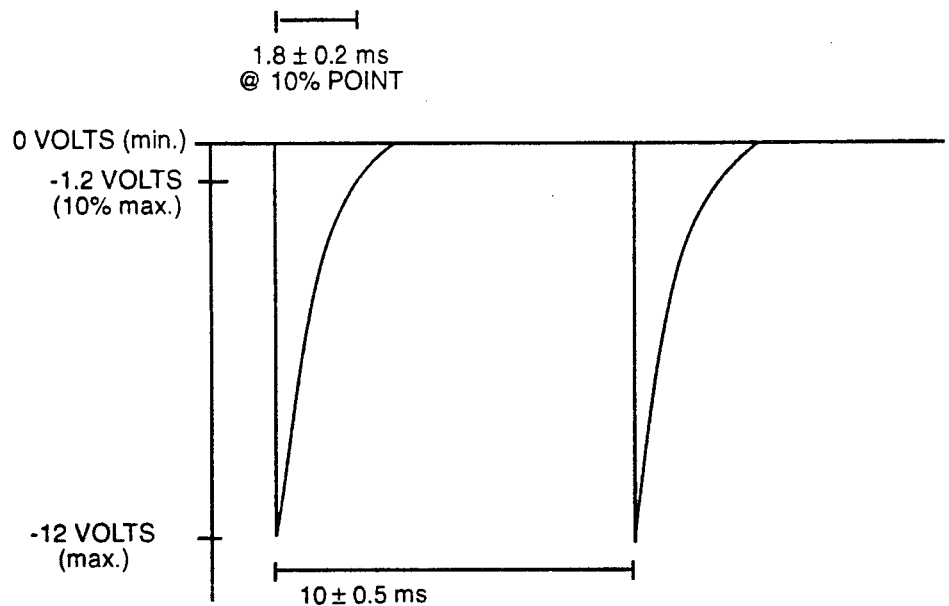
FIG. 3 is a voltage waveform illustrating the characteristics of the electrical treatment signal under no load condition as produced by the electrical stimulator apparatus.

As may be seen from a consideration of the block diagram of FIG. 1 illustrating the electrical stimulator apparatus for implementing my method of treating osteoarthritis, the stimulator includes a relaxation oscillator 1 with the output thereof differentiated at 2 so as to repetitively produce spiked negative going R-C time constant type pulses of the nature illustrated in FIG. 3. Such voltage pulses repeat within the frequency range of 90–110 hertz.

Such differentiated output voltage pulses are connected to an attenuator 3 for varying the output level of such pulses from zero to the maximum battery voltage minus approximately 2 volts. That is to say, the use of a 12 volt battery will allow the production of maximum amplitude pulses of approximately $-10$ volts. The output of the attenuator in turn is buffered by a unity gain push-pull transistor output stage 4, which in turn is coupled to the output leads by a large capacitor 5 and a DC restorer circuit 6. The capacitive output stage is designed so as to prevent the application of full battery voltage on the output leads in the event that the oscillator or amplifier section should fail. Additionally, as may be seen from FIG. 1, the electrical stimulator is powered by battery 7 by way of power switch 8.

Figure 2:
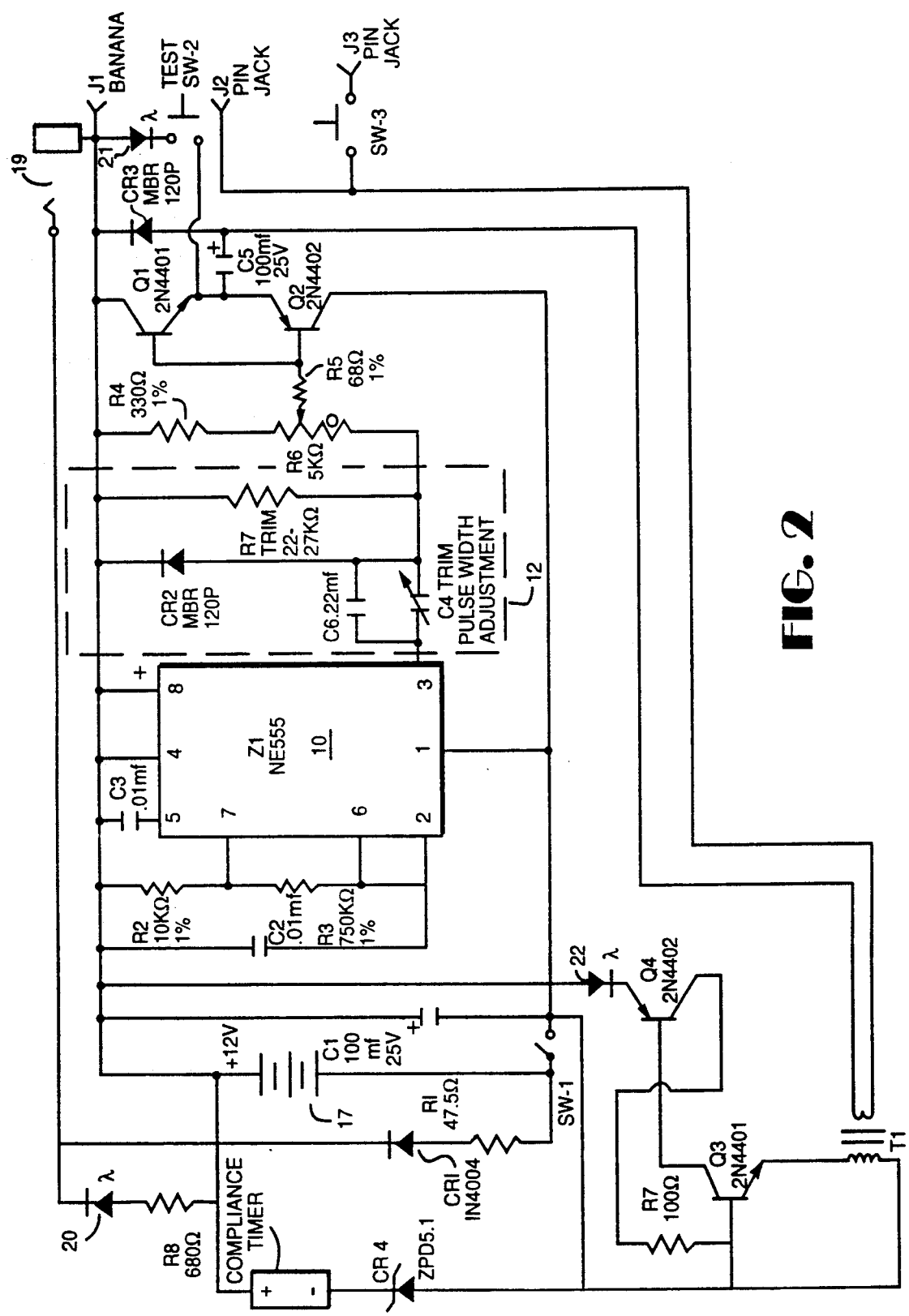
FIG. 2 is a more detailed schematic diagram of a presently preferred embodiment of my electrical stimulator apparatus.

As implemented for clinical testing, the elements of FIG. 1 include the components as detailed in FIG. 2. For example, the relaxation oscillator may include a conventional integrated circuit 10 for generating a pulsed output which is shaped by the associated capacitors, resistors and diode of differentiator 12. The amplitude of the differentiated voltage output pulses are adjusted by way of the variable setting of potentiometer R6 with the output of the attenuator buffered by way of the unit gain transistor output stage comprising Q1 and Q2 followed by a capacitive output stage. The stimulator unit is powered by an internal 12 volt nickel-cadmium battery pack 17 by way of power switch SW-1.

As may be seen from FIG. 2, the battery pack may be charged by an external transformer (not shown) which is connected by way of the charger jack 19. The presence of a charging voltage is indicated through the use of a yellow LED 20. Moreover, the unit may be tested for an output voltage by momentarily closing test switch SW-2 which will activate a red LED 21 in the presence of an output voltage. Additionally, a complete circuit path through a patient is indicated by way of a green LED 22. When the electrical stimulator is turned on and a patient is connected to electrodes that are normally attached to output jacks J1 and J2, LED 22 is connected to the output jacks by way of the series connected input winding of transformer T1 with the secondary winding connected to an amplifier stage comprising transistors Q3 and Q4.

The stimulator circuit shown in FIG. 2 is illustrative of two types of such stimulators identified as "active" and "inactive" as used in the carefully controlled double-blinded clinical trials. That is to say, as used in the clinical study both types of stimulators were essentially the same except that the "active" patients were connected to the stimulator by way of output jacks J1 and J2 and the "inactive" patients were connected to the stimulator by jacks J1 and J3. Both units contained the switch SW-3 that was used by the patient during the set up period. During the clinical studies patients were instructed to turn the stimulator on and to depress switch SW-3 while turning the output to a level that was felt by the individual patient. Thereafter, the patient was instructed to slowly reduce the output level to one which was not felt at which point the switch SW-3 was to be released. The patient was additionally told that there should be no change in sensation when the switch was pressed and released and that if a change was felt the stimulator should be further reduced so that no change in sensation was detected for either position of the switch.

As may be seen from FIG. 2, patients using the "inactive" stimulators with electrodes attached to output jacks J1 and J3 would not receive any electrical signal after switch SW-3 was released. Whereas, patients using "active" stimulators received an electrical signal at a subsensory level when SW-3 was released since for "active" patients the electrodes were connected to output jacks J1 and J2. Thus, the design allowed for a "placebo" treatment of patients with "inactive" stimulators, as well as an active treatment of patients with "active" stimulators. Moreover, the placebo devices physically looked and functioned like the active devices including the production of the stimulator output during the set up period. Thereafter, however, when SW-3 was released at the end of the set up process, no electrical stimulation was produced at the electrode outputs of inactive devices. Accordingly, each placebo control patient wore a device which provided no electrical stimulation during the treatment time.

Prior to the above noted clinical trials in humans, a confidential Premarket Approval Application was filed with the U.S. Food and Drug Administration summarizing research on animal models wherein the research had clear implications for the treatment of arthritis in humans. The application and research results presented indicated that the stimulator device used was both safe for animals and had the potential to treat injuries and diseases involving cartilage damage such as osteoarthritis. These studies combined with previous work of others using different electrical signals resulted in an approved FDA Investigational Device Exemption which permitted human clinical studies of osteoarthritis and rheumatoid arthritis to be conducted using the disclosed simulator system.

Thereafter, clinical investigation of the disclosed system was carried out in five medical centers using both active and placebo devices which were visually indistinguishable from one another. Moreover, the investigation was conducted using the double-blind technique wherein neither the patients nor the physicians were aware of which units were active or placebo devices, and the devices were randomly distributed. Within each sequence of ten devices there are five active and five placebo. The ten devices were given to patients on a randomized basis and neither the patient nor the physician was made aware of which devices were active.

Patients with osteoarthritis in at least one knee were qualified by their treating physician using criteria whereby the patient was required to be over twenty years of age with degenerative joint disease supported by radiographic and clinical evidence of same. Moreover, patients were expected to maintain their current medication throughout the study interval. The study interval was eight weeks in length with the first two weeks used for pretreatment base line observations. Thereafter, the device (active or placebo) was to be used daily for the next four weeks with a two week post-treatment follow-up interval for the detection and observation of adverse reactions if any.

Figure 4:
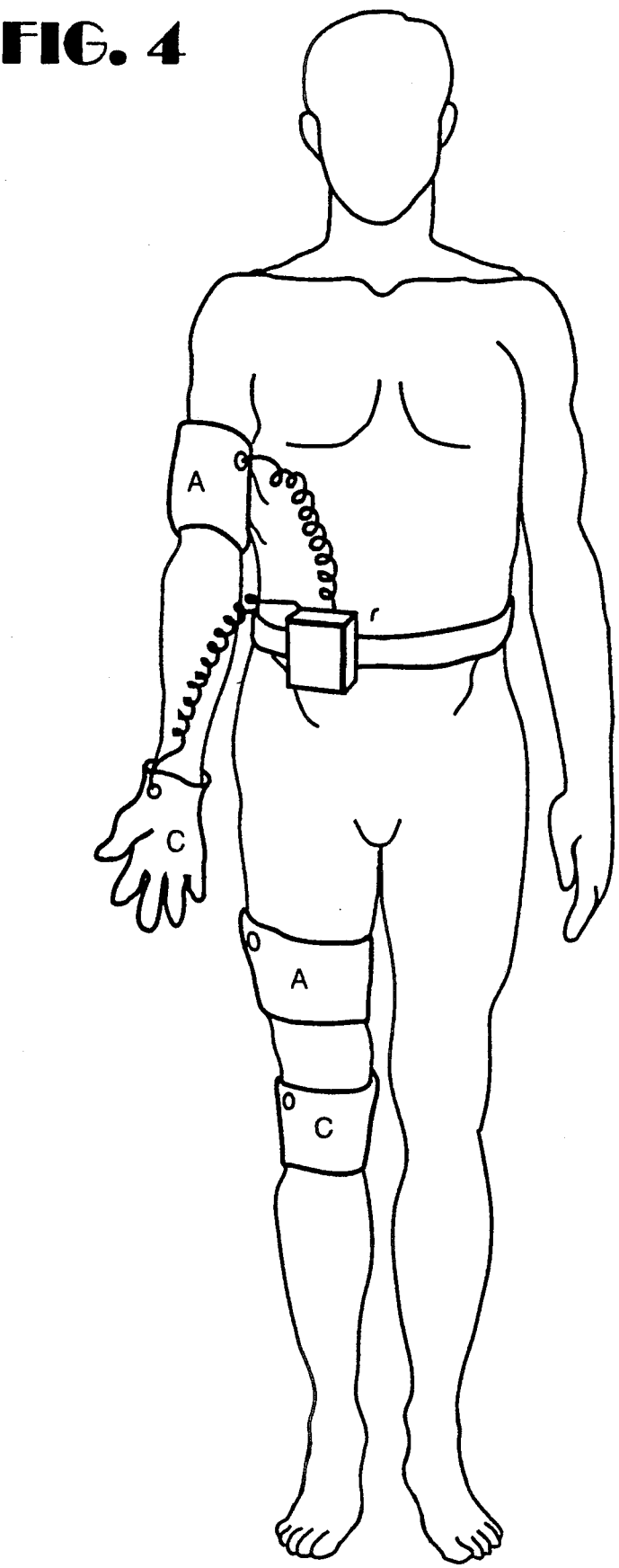
FIG. 4 illustrates two examples of electrode placement in the treatment of osteoarthritic joints.

Treatment consisted of a portable battery operated device with non-invasive electrodes applied to the designated knee daily for four weeks. Placement of the electrodes for the knee was as shown in one of the two examples illustrated in FIG. 4 wherein the negative electrode (C) was placed over the osteoarthritic knee joint with the positive electrode "A" placed on the same limb proximal to the negative electrode.

Patients were instructed in the proper use of the device as described above and were told to use the devices for six to ten hours per day. The devices were generally worn during the night while the patient was asleep. As previously noted, the placebo device looked and seemingly functioned like the active device including the production of the sensation for setting the stimulation level for each instance of use.

The five medical centers summarized in this study provided data for 41 patients in the active group and 37 patients in the placebo group. Evaluable patient counts are: active device 38 patients and placebo device 33 patients. Two patients on the active device and four patients on the placebo device dropped out early in the treatment phase of the study. One additional patient on the active device completed the study with favorable results, however, this patient did not have a matching placebo control in this data set and was not included in the analysis.

There were three primary efficacy criteria reported on standardized ten centimeter visual analog scales marked with numbers 0 to 10 to indicate scores of increasing numerical severity. These criteria are: physician overall evaluation, patient evaluation of function of the treated knee and patient evaluation of pain in the treated knee. These efficacy criteria were expressed as scores and as percent change from baseline. Statistically significant differences for all primary efficacy criteria favored the disclosed stimulator therapy in the three and four week treatment data.

Percent change from baseline data were expanded to present frequency distributions showing counts of patients who experienced ranked categories of percent change for each primary efficacy criterion. Changes of 50 percent or greater were defined as marked clinical improvement. These qualitative data were combined to develop new frequency distributions showing counts of patients with 3, 2, 1 or 0 criteria with a change of 50 percent or greater. One objective was to provide a single predictive index for physicians. For the active device, one-half of the patients experienced marked clinical improvement in at least one primary efficacy criterion compared to only one-third in the placebo device group. Approximately one-fourth of the active device treated patients experienced marked clinical improvement in all three primary efficacy criteria compared to only six percent in the placebo device group. The comparison between the active and placebo device frequency distributions was statistically significant ($P < 0.05$).

This study also included average responses for several secondary efficacy criteria. The treating physicians evaluated tenderness, swelling, circumference, range of motion, extension and walking time. Tenderness and swelling did not provide discrimination between groups. Circumference of the treated knee, however, improved with a mean decrease of −0.30 inches in the active device treated group in contrast to the placebo device treated group that worsened with a mean increase of +0.13 inches. Walking time was not significantly different between groups and would not be expected to be so because the study treated only one knee and walking time is a function of both knees and hips. The range of knee motion as measured by flexion, showed an improvement for patients treated with the active device compared to the placebo device patients. A frequency distribution analysis of knee flexion showed degrees of improvement that were statistically significant in favor of the active device treated patients. All three secondary efficacy criteria evaluated by the patients, (general morning stiffness, stiffness of the treated knee and overall symptoms) showed trends favoring the active device. The analysis of morning stiffness in minutes showed a mean improvement of 20 minutes in the active device treated patients compared to a one minute increase in morning stiffness in the placebo device patients. Moreover, results for the duration of morning stiffness in the treated knee were expanded to show frequency distributions for three ranked time intervals that support a statistically significant ($P \leq 0.05$) active versus placebo comparison.

Approximately equal percentages of patients on active and placebo devices (20%) reported experiencing a transient and mild skin rash at the electrode location. The skin rash reported here is comparable to that reported by other FDA approved electrical stimulators for non-union fractures and for scoloisis. The rash prompted one active device patient and one placebo device patient to discontinue their study participation. One patient on an active device reported a single episode of diarrhea. There were no new adverse reactions reported in the two week follow-up interval after treatment.

Three of the medical centers treated private practice patients, and the two veterans' medical centers treated veterans only. All of the efficacy data analyses were carried out for the full data set (five centers) and most were carried out for the private practice patients (3 centers).

In summary, the two basic objectives of this clinical investigation were clearly met. The disclosed method and apparatus can decrease pain and improve joint function in patients with osteoarthritis of the knee. This is supported by statistical and clinically meaningful improvement in the efficacy criterion that measured change in the most widely recognized clinical features of joint pain, stiffness and limitation of motion. In addition, the adverse reactions that were reported during the clinical investigation were transient and resolved spontaneously following diagnosis and correction of the underlying cause or immediately following completion of treatment. All of these findings are the result of this five-center double blinded, randomized, clinical investigation that utilized a concurrent placebo device control.

The analysis of this carefully controlled clinical investigation provides valid scientific evidence that the disclosed method and stimulator are safe and effective for use in treating patients with osteoarthritis of the knee. More specifically, this device is indicated for use in relieving pain and improving function in patients with osteoarthritis of the knee.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of treating arthritic joint symptoms including joint stiffness, range of motion and pain, said method comprising the steps of:
   applying electrical impulses via non-invasive conductive electrodes in contact with a patient's skin proximate to said joint, the amplitude of said impulses initially being sufficiently high as to be sensed by said patient;
   reducing only the amplitude of said impulses to a level that is subsensory as to said patient; and
   continuing the application of said impulses at said reduced amplitude and with no adjustment to the widths of said impulses for the remainder of a treatment period.

2. A method as in claim 1 wherein said impulses once reduced are maintained as constant amplitude unidirectional voltage pulses.

3. A method as in claim 1 wherein said arthritic joint symptoms are osteoarthritis symptoms which include pain, joint stiffness, limitation of range of motion as well as limitation of overall function.

4. A method as in claim 1 wherein as a result of said reducing step the amplitude of said impulses are just below the level at which the patient can sense said impulses.

5. A method of treating arthritic joint symptoms, said method comprising the steps of:
   applying electrical impulses via non-invasive conductive electrodes in contact with a patient's skin proximate to said joint, the amplitude of said impulses being sufficiently high as to be sensed by said patient;
   reducing the amplitude of said impulses to a level that is subsensory as to said patient; and
   continuing the application of said impulses at said reduced amplitude for the remainder of a treatment period and wherein said impulses are spiked negative unidirectional voltage pulses.

6. A method as in claim 5 wherein said reducing step is obtained by an attenuator which can vary the output level from 0 volts to a maximum of about −10 volts.

7. A method as in claim 5 wherein the frequency of said impulses is within the range of 90 to about 110 hertz.

8. A method of treating arthritic joint symptoms, said method comprising the steps of:
   applying electrical impulses via non-invasive conductive electrodes in contact with a patient's skin proximate to said joint, the amplitude of said impulses being sufficiently high as to be sensed by said patient;
   reducing the amplitude of said impulses to a level that is subsensory as to said patient; and
   continuing the application of said impulses at said reduced amplitude for the remainder of a treatment period and wherein said treatment period is about 8 hours per day.

9. An apparatus for treating arthritic joint symptoms including joint stiffness, range of motion and pain, said apparatus comprising:
   non-invasive conductive electrode means for contacting a patient's skin proximate said joint;

pulse generating means connected to said electrode means for producing constant amplitude unidirectional voltage pulses at a frequency in the range of 90 to 110 hertz and at an amplitude just below the sensory level of said patient, whereby said pulses are applied to a patient for a predetermined treatment period, and wherein said pulses are spiked negative unidirectional pulses.

10. An apparatus as in claim 9 wherein said arthritic joint symptoms are osteoarthritis symptoms which include pain, joint stiffness, limitation of range of motion as well as limitation of overall function.

11. An apparatus as in claim 10 wherein said pulse generating means includes an oscillator means, a pulse shaping means connected to said oscillator means and an attenuator means connected to said pulse shaping means for producing said pulses at said constant amplitude just below the sensory level of said patient.

12. An apparatus as in claim 11 further including a capacitive output stage for preventing excessive voltage levels from being applied to said electrodes.

13. An apparatus as in claim 9 wherein said predetermined treatment period is about 8 hours per day.

* * * * *